(12) United States Patent
Gosnell et al.

(10) Patent No.: US 8,075,925 B2
(45) Date of Patent: Dec. 13, 2011

(54) PRODUCTION OF CANOLA PROTEIN

(75) Inventors: Brandy Gosnell, Winnipeg (CA); Kevin I. Segall, Winnipeg (CA); Martin Schweizer, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 40 days.

(21) Appl. No.: 11/922,890

(22) PCT Filed: Jun. 30, 2006

(86) PCT No.: PCT/CA2006/001084
§ 371 (c)(1),
(2), (4) Date: Apr. 7, 2009

(87) PCT Pub. No.: WO2007/003044
PCT Pub. Date: Jan. 11, 2007

(65) Prior Publication Data
US 2009/0203880 A1  Aug. 13, 2009

Related U.S. Application Data

(60) Provisional application No. 60/695,535, filed on Jul. 1, 2005.

(51) Int. Cl.
*A61K 36/00* (2006.01)
(52) U.S. Cl. .......................... 424/725; 424/776
(58) Field of Classification Search .................. None
See application file for complete search history.

(56) References Cited

U.S. PATENT DOCUMENTS

| | | | |
|---|---|---|---|
| 4,418,013 A | 11/1983 | Cameron et al. | |
| 4,889,921 A | 12/1989 | Diosady et al. | |
| 5,844,086 A * | 12/1998 | Murray | 530/377 |
| 6,005,076 A * | 12/1999 | Murray | 530/377 |
| 2003/0125526 A1 | 7/2003 | Barker et al. | |
| 2004/0034204 A1 | 2/2004 | Benhoff et al. | |
| 2004/0039174 A1 | 2/2004 | Barker et al. | |
| 2004/0254353 A1 | 12/2004 | Barker et al. | |
| 2005/0181112 A1 | 8/2005 | Schweizer et al. | |
| 2005/0202154 A1 | 9/2005 | Diosady et al. | |

FOREIGN PATENT DOCUMENTS

| | | |
|---|---|---|
| GB | 2077739 | 12/1981 |
| JP | 543597 | 2/1993 |
| WO | WO 02/089597 | 11/2002 |
| WO | WO 03/043439 | 5/2003 |
| WO | WO 03/088760 | 10/2003 |
| WO | WO 2005/067729 | 7/2005 |

OTHER PUBLICATIONS

Murray et al; "Rapeseed: A Potential Global Source of High Quality Plant Protein". Asian Pacific Food Industry, AP Trade, Apr. 2001, pp. 30-34.

* cited by examiner

*Primary Examiner* — Christopher R Tate
*Assistant Examiner* — Randall Winston
(74) *Attorney, Agent, or Firm* — Michael I. Stewart; Sim & McBurney

(57) ABSTRACT

A canola protein isolate having a protein content of at least about 90 wt % (N×6.25), preferably at least about 100 wt %, and consisting predominantly of the 2S protein and substantially free from the 7S and 12S proteins is prepared. In one aspect, canola oil seed meal is extracted with aqueous protein solution at an elevated temperature to preferentially extract 2S protein from the meal to produce a canola protein solution containing predominantly 2S protein. The 2S canola protein is recovered as an isolate. In another aspect, canola oil seed meal is initially extracted with water to preferentially extract 7S and 12S canola proteins followed by extraction of the canola oil seed meal with aqueous saline solution to extract 2S protein from the meal. 2S canola protein isolate is recovered from the saline extract. In another aspect, the canola oil seed meal is extracted with aqueous saline solution to extract 2S, 7S and 12S proteins from the meal. The aqueous protein extract solution is heat treated at an elevated temperature to precipitate 7S and 12S proteins and leave a 2S protein solution from which the isolate may be recovered. In a further aspect, the aqueous protein solution is concentrated prior to the heat treatment.

15 Claims, No Drawings

PRODUCTION OF CANOLA PROTEIN

REFERENCE TO RELATED APPLICATION

This application claims priority under 35 USC 119(e) from U.S. Provisional Patent Application No. 60/695,535 filed Jul. 1, 2005.

FIELD OF INVENTION

The present invention relates to novel procedures for the preparation of the 2S protein of canola, substantially free from the 7S and 12S proteins of canola.

BACKGROUND TO THE INVENTION

Canola protein isolates can be formed from canola oil seed meal. In copending U.S. patent application Ser. Nos. 10/137,391 filed May 3, 2002 (US Patent Application Publication No. 20030125526A1), 10/476,230 filed Jun. 9, 2004 (US Patent Application Publication No. 20040254353A1) and corresponding PCT Publication No. WO 02/089597, both assigned to the assignee hereof and the disclosures of which are incorporated herein by reference, there is described a method of making canola protein isolates from canola oil seed meal, such isolates having at least 100 wt % protein content (N×6.25). The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous gluten-like protein micellar mass (PMM), and recovering the protein micellar mass from supernatant having a protein content of at least about 100 wt % as determined by Kjeldahl nitrogen (N×6.25). As used herein, protein content is determined on a dry weight basis. The recovered PMM may be dried.

In one embodiment of the process described above, the supernatant from the PMM settling step is processed to recover a protein isolate comprising dried protein from the wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt % of protein (N×6.25), preferably at least about 100 wt % protein (N×6.25).

In another embodiment of the process described above, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt % protein (N×6.25), preferably at least about 100 wt % protein (N×6.25).

The procedures described in the aforementioned US patent applications are essentially batch procedures. In copending U.S. patent application Ser. No. 10/298,678 filed Nov. 19, 2002 (US Patent Application Publication No. 20040039174A1) and corresponding published International Application No. WO 03/043439, assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % as determined by Kjeldahl nitrogen (N×6.25), preferably at least about 100 wt % (N×6.25).

As described in the aforementioned U.S. patent application Ser. Nos. 10/137,391 and 10/471,230, the overflowed supernatant may be processed to recover canola protein isolate therefrom.

Canola seed is known to contain about 10 to about 30 wt % proteins and several different protein components have been identified. These proteins are distinguished by different sedimentation coefficients (S). These known and identified proteins include a 12S globulin, known as cruciferin, and a 2S storage protein, known as napin.

Canola is Also Known as Rapeseed or Oil Seed Rape

In copending U.S. patent application Ser. Nos. 10/413,371 filed Aug. 25, 2003 (US Patent Application Publication No. 20040034204) and 10/510,766 filed Apr. 15, 2003 as well as the corresponding published PCT Publication No. WO 03/08876 assigned to the assignee hereof and the disclosure of which is incorporated herein by reference, there is described the composition of the PMM canola protein isolate and of the supernatant-derived canola protein isolate. The supernatant-derived canola protein isolate is comprised mostly of the 2S protein with smaller amounts of 7S protein and a trace amount of 12S protein. The 2S protein is a low molecular weight albumin. The PMM produced is comprised predominantly of the 7S protein with 2S protein and 12S protein being relatively minor components. The 7S and 12S protein are higher molecular weight globulins with the 7S molecule being the half molecule of the 12S protein.

As described therein, the supernatant-derived canola protein isolate exhibits a protein profile which is:
  about 60 to about 95% wt % of 2S protein,
  about 5 to about 40 wt % of 7S protein, and
  0 to about 5 wt % of 12S protein, preferably
  about 70 to about 95 wt % of 2S protein,
  about 5 to about 30 wt % of 7S protein, and
  0 to about 2 wt % of 12S protein.

The PMM canola protein isolate exhibits a protein profile which is:
  about 60 to about 98 wt %, of 7S protein,
  about 1 to about 15 wt % of 12S protein, and
  0 to about 25 wt % of 2S protein, preferably
  about 88 to about 98 wt % of 7S protein,
  about 1 to about 10 wt % of 12S protein, and
  0 to about 6 wt % of 2S protein.

It has been found that the supernatant-derived canola protein isolate consisting predominantly of 2S protein exhibits superior functional properties for certain applications than the PMM-derived canola protein isolate consisting predominantly of 7S protein. In the procedures described in the prior applications, in order to produce the supernatant-derived canola protein isolate, it was necessary to go through the steps of PMM formation and provision of a supernatant in order, in effect, to fractionate the canola proteins.

In U.S. patent application Ser. No. 11/038,086 filed Jul. 21, 2005 (U.S. Patent Application Publication No. US 2005-0181112A1), assigned to the assignee hereof and the disclosure of which is incorporated herein by reference (WO 2005/067729), there is described a procedure in which the supernatant from the PMM precipitation is, following membrane processing, subjected to heat treatment to precipitate the 7S protein and leave a protein solution enriched in 2S protein. The remaining solution may be spray dried.

The 2S protein having a minimal proportion of the 7S and 12S proteins demonstrates increased solubility over the untreated 2S protein at acid pH values and is able to provide improved clarity in solution and with soft drinks, providing clear protein fortified beverages.

SUMMARY OF INVENTION

It has been surprisingly found that, according to one aspect of the present invention, if the extraction of the canola oil seed meal is effected at an elevated temperature, rather than at relatively ambient temperatures, then the 2S protein is extracted preferentially to the 7S and 12S proteins and the canola protein in the resulting extract solution consists predominantly of the 2S protein, which then can be obtained in relatively pure form from the extract solution.

While not wishing to be bound by any theory, it is believed that the ability to selectively extract 2S canola protein in preference to the 7S and/or 12S proteins at the elevated extraction temperature results from degradation and precipitation of the 7S and 12S proteins in the canola oil seed meal during the extraction step.

Accordingly, in one aspect of the present invention there is provided a method for production of a canola protein isolate consisting predominantly of the 2S canola protein, which comprises: extracting canola oil seed meal with an aqueous salt solution at an elevated temperature to preferentially extract the 2S protein from the canola oil seed meal in preference to the 7S and 12S proteins and to obtain a canola protein extract solution containing predominantly 2S protein, separating the canola protein extract solution from residual canola oil seed meal, and recovering from the canola protein extract solution a canola protein isolate having a protein content of at least about 90 wt % (N×6.25) and consisting predominantly of the 2S canola protein.

It has further been surprisingly found that, according to a further aspect of the present invention, if the canola oil seed meal extraction is effected in two stages, the first extraction being effected using water and the second using an aqueous salt solution, there is obtained from the first extraction step an aqueous canola protein solution which is predominantly the 7S protein and from the second extraction step an aqueous canola protein extract solution which is predominantly the 2S protein.

The initial extraction step of the canola oil seed meal with water solubilizates a notable proportion of the 7S and 12S proteins, a lower proportion of 2S protein and a major portion of the soluble impurities. The second extraction with aqueous saline solution, results in an aqueous canola protein solution containing a majority of 2S protein, minor amounts of 7S and 12S proteins and a low concentration of soluble impurities.

The aqueous saline canola protein extract is concentrated, diafiltered to reduce the salt content and then heat treated to precipitate the residual 7S and 12S proteins, in accordance with the procedure described in the aforementioned U.S. patent application Ser. No. 11/038,086.

According to this further aspect of the present invention, there is provided a method for the preparation of a canola protein isolate consisting predominantly of the 2S canola protein, which comprises: extracting canola oil seed meal with water to preferentially extract 7S and 12S canola proteins and soluble impurities in preference to the 2S protein, to form a first canola protein extract solution, separating the first canola protein extract solution from the residual oil seed meal, extracting the residual oil seed meal with an aqueous salt solution to dissolve 2S, 7S and 12S proteins from the residual oil seed meal to form a second canola protein extract solution, and recovering a canola protein isolate having a protein content of at least about 90 wt % (N×6.25) and consisting predominantly of 2S canola protein from the second canola protein extract solution.

It has further surprisingly been found, in accordance with another aspect of the present invention, that the concentrated canola protein solution from the concentration step described in the above-mentioned U.S. patent application Ser. No. 10/137,391 may be heat treated in accordance with the procedure of the aforementioned U.S. patent application Ser. No. 11/038,586 to precipitate the majority of the 7S and 12S proteins contained therein leaving a concentrated aqueous canola protein solution consisting substantially of 2S protein.

According to this additional aspect of the present invention, there is provided a method for the production of a canola protein isolate consisting predominantly of the 2S canola protein, which comprises: extracting canola oil seed meal with an aqueous salt solution to extract canola proteins from the canola oil seed meal and to obtain a canola protein solution, separating the canola protein solution from residual oil seed meal, concentrating said canola protein solution to provide a concentrated protein solution as a retentate, heat treating the concentrated protein solution to selectively precipitate 7S and 12S canola proteins from the concentrated canola protein solution in preference to 2S canola protein to form a heat-treated canola protein solution containing predominantly 2S canola protein, separating the heat-treated canola protein solution from the precipitated proteins, and recovering a canola protein isolate having a protein content of at least about 90 wt % (N×6.25) and consisting predominantly of 2S canola protein from the separated heat-treated canola protein solution.

It has further surprisingly found that, in accordance with a further aspect of the present invention, the aqueous canola protein solution obtained by salt extraction of the canola oil seed meal following the procedure of the above-mentioned U.S. patent application Ser. No. 10/137,391 may be heat treated in accordance with the procedure of the aforementioned U.S. patent application Ser. No. 11/038,586 to precipitate the majority of the 7S and 12S proteins contained therein leaving an aqueous canola protein solution consisting substantially of 2S protein.

According to this further aspect of the present invention, there is provided a method for the production of a canola protein isolate consisting predominantly of the 2S canola protein, which comprises: extracting canola oil seed meal with an aqueous salt solution to extract canola proteins from the canola oil seed meal and to obtain a canola protein solution, separating the canola protein solution from the residual oil seed meal, heat treating the concentrated protein solution to selectively precipitate 7S and 12S canola proteins in preference to 2S canola protein from the canola protein solution to form a heat-treated canola protein solution containing predominantly 2S canola protein, separating the heat-treated canola protein solution from the precipitated proteins, and recovering a canola protein isolate having a protein content of at least about 90 wt % (N×6.25) and consisting predominantly of 2S canola protein from the separated heat-treated canola protein solution.

The procedures of the present invention enable there to be obtained a canola protein isolate consisting predominantly of the 2S canola protein, without the necessity of employing the PMM-precipitating fractionation step, thereby greatly simplifying the procedure and enabling the 2S protein predominated canola protein isolate to be obtained more economically.

The canola protein isolates produced according to the processes herein may be used in conventional applications of protein isolates, such as, protein fortification of processed foods, emulsification of oils, body formers in baked goods and foaming agents in products which entrap gases. In addition, the canola protein isolates may be formed into protein fibers, useful in meat analogs, may be used as an egg white substitute or extender in food products where egg white is used as a binder. The canola protein isolate may be used as nutritional supplements. Other uses of the canola protein isolate are in protein-fortified beverages, pet foods, animal feed and in industrial and cosmetic applications and in personal care products.

GENERAL DESCRIPTION OF INVENTION

As described above, the present invention provides four aspects of a process for producing a canola protein solution consisting predominantly of 2S protein substantially free from 7S and 12S proteins.

(a) Aspect Utilizing High Temperature Extraction of Canola Oil Seed Meal

The initial step of the process of providing canola protein isolates according to this aspect of the invention involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization, in one aspect of the present invention, is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, up to about 0.2, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the canola oil seed meal chosen.

The extraction of the canola oil seed meal, in this aspect of the present invention, is effected at an elevated temperature, generally at a temperature of about 70° to about 100° C., preferably about 80° to about 95° C., to cause preferential extraction of 2S canola protein from the oil seed meal into the protein extract solution, in preference to 7S and 12S proteins.

The aqueous food grade salt solution generally has a pH of about 5 to about 6.8, preferably about 5.3 to about 6.2. The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of canola oil seed meal in the food grade salt solution during the solubilization step may vary widely. Typical concentration values are about 5 to about 15% w/v.

The protein solution resulting from the extraction step generally has a protein concentration of about 1 to about 40 g/L, preferably about 10 to about 20 g/L.

The protein solution generally has a canola protein profile which is:
about 80 to about 100 wt % 2S protein,
0 to about 10 wt % 7S protein, and
0 to about 10 wt % 12S protein;
preferably about 85 to about 100 wt % 2S protein,
0 to about 15 wt % 7S protein, and
0 to about 5 wt % 12S protein.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

The aqueous protein extract solution is processed to recover the canola protein isolate therefrom. The canola protein isolate produced herein has a protein content of at least about 90 wt % (N×6.25), preferably at least about 100 wt %, and consists predominantly of the 2S protein.

In such processing, the protein extract solution may be concentrated to increase the protein concentration thereof.

Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the protein extract solution in this way also reduces the volume of liquid required to be dried to recover the protein. The protein extract solution generally is concentrated to a protein concentration of at least about 50 g/L, preferably about 100 to about 400 g/L, more preferably about 200 to about 300 g/L. Such concentration operation may be carried out in a batch mode or in a continuous operation.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors. The molecular weight cut-off of the membrane is usually chosen to ensure retention of a significant proportion of the protein in the solution, while permitting contaminants to pass through having regard to the different membrane materials and configurations.

The concentrated protein extract solution then may be subjected to a diafiltration step using water. Such diafiltration may be effected using from about 2 to about 20 volumes of diafiltration solution, preferably about 5 to about 10 volumes of diafiltration solution. In the diafiltration operation, further quantities of contaminants are removed from the aqueous protein extract solution by passage through the membrane with the permeate. The diafiltration operation may be effected until no significant further quantities of phenolics and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated protein extract solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour absorbing agent is polyvinyl pyrrolidone.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour absorbing agent, an amount of about 0.5% to about 5% w/v, preferably about 2% to about 3% w/v, may be used. The colour absorbing agent may be removed from the canola protein solution by any convenient means, such as by filtration.

If desired, the concentrated and optionally diafiltered aqueous protein solution may be subjected to a heat-treatment step to reduce the quantity of 7S and 12S proteins present in the solution. Such heat treatment may be effected using a temperature and time profile sufficient to decrease the proportion of 7S and 12S present in the solution, preferably to reduce the proportion of 7S and 12S proteins by a significant extent. In general, the 7S and 12S protein content of the solution is reduced by at least about 50 wt %, preferably at least about 75 wt %, by the heat treatment. In general, the heat treatment may be effected at a temperature of about 70° to about 100° C., preferably about 75 to about 95° C., for about 2 to about 30 minutes, preferably about 5 to about 15 minutes. The precipitated 7S and 12S proteins may be removed and recovered in any convenient manner, such as by centrifugation or filtration.

The concentrated and optionally diafiltered and optionally heat-treated aqueous protein solution may be dried by any convenient technique, such as spray drying or freeze drying, to a dry form to provide a dried canola protein isolate which consists predominantly of 2S canola protein and which has a protein content of at least about 90 wt % (N×6.25), preferably at least 100 wt %.

(b) Aspect Utilizing Multiple Extractions of Canola Oil Seed Meal

The initial step of the process of providing canola protein isolates involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization in this aspect of the present invention is effected in multiple steps. In a first step, water is employed as the extraction medium, which preferentially extracts the 7S and 12S canola proteins from the canola oil seed meal and in preference to the 2S canola protein along with a sizable proportions of the soluble impurities. The water extraction step may be effected as a single water extraction of the canola oil seed meal or multiple water extractions of the canola oil seed meal, such as from about 2 to about 25 extractions, preferably about 2 to about 4 extractions.

The aqueous solution of 7S and 12S proteins may be processed in any desired manner to recover the 7S and 12S proteins as a canola protein isolate. For example, the aqueous protein solution, after addition of saline, may be subjected to the concentration and micelle formation steps as described in the aforementioned U.S. patent application Ser. No. 10/137, 391. The extraction of the canola oil seed meal using water may be effected at a temperature of about 10° to about 70° C., preferably about 55° C. to about 65° C. The concentration of canola oil seed meal in the water during the solubilization step may vary widely. The typical concentration values are about 5 to about 15% w/v.

The protein solution resulting from the aqueous extract step generally has a protein concentration of about 10 to about 40 g/L, preferably about 10 to about 25 g/L.

In the second step of solubilization, the residual canola oil seed meal from the water extraction(s) is extracted with an aqueous salt solution which results in an aqueous canola protein extraction solution containing a majority of 2S canola protein, minor amounts of 7S and 12S canola protein and a low level of impurities. The salt usually is sodium chloride, although other salts, such as sodium chloride may be used. A food grade salt solution generally is used, but where the canola protein isolate is intended for non-food uses, non-food grade chemicals may be used.

The aqueous salt solution used in the second step of solubilization generally has an ionic strength of at least about 0.05, preferably at least about 0.1, generally up to about 0.5.

The aqueous food grade salt solution generally has a pH of about 5 to about 6.8, preferably about 5.3 to about 6.2, the pH of the salt solution may be adjusted to any desired value within the range of about 5 to about 6.8 for use in the extraction step by the use of any convenient acid, usually hydrochloric acid, or alkali, usually sodium hydroxide, as required.

The extraction of the above-cited canola oil seed meal with the food grade salt solution is generally carried out at a temperature of about 5° to about 65° C., preferably about 20° to about 30° C. The concentration of canola oil seed meal in the food grade salt solution during the solubilization step may vary widely, generally about 5 to about 15% w/v.

The protein solution resulting from the saline extraction step generally has a protein concentration of about 1 to about 40 g/L, preferably about 5 to about 20 g/L.

The aqueous protein solution resulting from the saline solubilization of the oil seed meal generally has a canola protein profile which is:
about 80 to about 100 wt % 2S protein,
0 to about 10 wt % 7S protein, and
0 to about 10 wt % 12S protein;
preferably about 85 to about 100 wt % 2S protein,
0 to about 15 wt % 7S protein, and
0 to about 5 wt % 12S protein.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

The aqueous canola protein solution may be processed to recover the canola protein isolate having a protein concentration of at least about 90 wt % (N×6.25), preferably at least about 100 wt % and consisting predominantly of the 2S protein.

In such processing, the protein extract solution may be concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the protein extract solution in this way also reduces the volume of liquid required to be dried to recover the protein. The protein extract solution generally is concentrated to a protein concentration of at least about 50 g/L, preferably about 100 to about 400 g/L, more preferably about 200 to about 300 g/L. Such concentration operation may be carried out in a batch mode or in a continuous operation.

The concentrated protein extract solution then may be subjected to a diafiltration step using water. Such diafiltration may be effected using from about 2 to about 20 volumes of diafiltration solution, preferably about 5 to about 10 volumes of diafiltration solution. In the diafiltration operation, further quantities of contaminants are removed from the aqueous protein extract solution by passage through the membrane with the permeate. The diafiltration operation may be effected until no significant further quantities of phenolics and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated protein extract solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

If desired, the concentrated and optionally diafiltered aqueous protein solution may be subjected to a heat-treatment step to reduce the quantity of 7S and 12S proteins present in the solution. Such heat treatment may be effected using a temperature and time profile sufficient to decrease the proportion of 7S and 12S present in the solution, preferably to reduce the proportion of 7S protein by a significant extent. In general, the 7S protein content of the solution is reduced by at least about 50 wt %, preferably at least about 75 wt % by the heat treatment. In general, the heat treatment may be effected at a temperature of about 70° to about 100° C., preferably about 75 to about 95° C., for about 2 to about 30 minutes, preferably about 5 to about 15 minutes. The precipitated 7S and 12S proteins may be removed in any convenient manner, such as by centrifugation or filtration.

The concentrated and optionally diafiltered and optionally heat-treated aqueous protein solution may be dried by any convenient technique, such as spray drying or freeze drying, to a dry form to provide a dried canola protein isolate which consists predominantly of 2S canola protein and which has a protein content of at least about 90 wt %, preferably at least about 100 wt %

(c) Aspect Utilizing Heat Treatment of Ultrafiltration Retentate

The initial step of the process of providing canola protein isolates involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as potassium chloride, may be used. The salt solution has an ionic strength of at least about 0.05, preferably at least about 0.10, up to about 0.2, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effected at elevated temperatures, preferably above about 35° C., generally up to about 65° C.

The aqueous salt solution and the canola oil seed meal have a natural pH of about 5 to about 6.8, pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required. Where the canola protein isolate is intended for non-food uses, then non-food grade chemicals may be used.

The concentration of oil seed meal in the salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous phase resulting from the extraction step then may be separated from the residual canola meal, in any convenient manner, such as by employing decanter centrifugation followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration of the separated aqueous protein solution, before or after concentration, as described below, also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee thereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a colour removal step and/or a first fat removal step is carried out, the salt generally is added after completion of such operations.

The protein extract solution is concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the protein extract solution in this way also reduces the volume of liquid required to be dried to recover the protein. The protein extract solution generally is concentrated to a protein concentration of at least about 50 g/L, preferably about 100 to about 400 g/L, more preferably about 200 to about 300 g/L. Such concentration operation may be carried out in a batch mode or in a continuous operation.

The concentrated protein extract solution then may be subjected to a diafiltration step using water. Such diafiltration may be effected using from about 2 to about 20 volumes of diafiltration solution, preferably about 5 to about 10 volumes of diafiltration solution. In the diafiltration operation, further quantities of contaminants are removed from the aqueous protein extract solution by passage through the membrane with the permeate. The diafiltration operation may be effected until no significant further quantities of phenolics and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated protein extract solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

In this aspect of the present invention, the ultrafiltered and optionally diafiltered canola protein solution is subjected to heat treatment to precipitate 7S and 12S proteins therefrom and leave a canola protein solution consisting predominately of 2S protein. Such heat treatment may be effected under the conditions described in the aforementioned U.S. patent application Ser. No. 11/038,086.

Such heat treatment may be effected using a temperature and time profile sufficient to decrease the proportion of 7S and 12S present in the concentrated solution, preferably to reduce the proportion of 7S and 12S proteins by a significant extent. In general, the 7S and 12S protein content of the solution is reduced by at least about 50 wt %, preferably at least about 75 wt % by the heat treatment. In general, the heat treatment may be effected at a temperature of about 70° to about 100° C., preferably about 75 to about 95° C., for about 2 to about 30 minutes, preferably about 5 to about 15 minutes. The precipitated 7S and 12S proteins may be removed and recovered in any convenient manner, such as centrifugation or filtration.

The resulting canola protein solution then may be processed to recover the 2S predominated canola protein isolate.

The concentrated heat-treated supernatant, after removal of the precipitated 7S and 12S proteins, such as by centrifugation, may be dried by any convenient technique, such as spray drying or freeze drying, to a dry form to provide a canola protein isolate which consist predominantly of the 2S canola protein. Such canola protein isolate has a high protein content, in excess of about 90 wt %, preferably at least about 100 wt % protein (calculated as Kjeldahl N×6.25) and is substantially undenatured (as determined by differential scanning calorimetry).

(d) Aspect Utilizing Heat Treatment of Aqueous Canola Protein Solution

The initial step of the process of providing canola protein isolates involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, up to about 0.2, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effected at elevated temperatures, preferably above about 35° C., generally up to about 65° C.

The aqueous salt solution and the canola oil seed meal have a natural pH of about 5 to about 6.8 pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required. Where the canola protein isolate is intended for non-food uses, then non-food grade chemicals may be used.

The concentration of oil seed meal in the salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous phase resulting from the extraction step then may be separated from the residual canola meal, in any convenient manner, such as by employing decanter centrifugation followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration of the separated aqueous protein solution, before or after concentration, as described below, also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee thereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a colour removal step and/or a first fat removal step is carried out, the salt generally is added after completion of such operations.

The aqueous canola protein solution in accordance with this aspect of the present invention, is heat-treated to precipitate 7S and 12S proteins therefrom and leave a canola protein solution in which the canola protein consists predominantly of 2S protein. Such heat treatment may be effected under the condition described in the aforementioned U.S. patent application Ser. No. 11/038,086.

Such heat treatment may be effected using a temperature and time profile sufficient to decrease the proportion of 7S and 12S present in the concentrated solution, preferably to reduce the proportion of 7S and 12S proteins by a significant extent. In general, the 7S and 12S protein content of the solution is reduced by at least about 50 wt %, preferably at least about 75 wt % by the heat treatment. In general, the heat treatment may be effected at a temperature of about 70° to about 100° C., preferably about 75 to about 95° C., for about 2 to about 30 minutes, preferably about 5 to about 15 minutes. The precipitated 7S and 12S proteins may be removed and recovered in any convenient manner, such as centrifugation or filtration.

The heat-treated canola protein solution, after removal of the precipitated 7S and 12S proteins, such as by centrifugation, may be dried by any convenient technique, such as spray drying or freeze drying to a dry form to provide a canola protein isolate consisting predominantly of 2S canola protein.

Alternatively, the heat-treated canola protein solution may be subjected to the concentration, diafiltration and colour removal steps described above with respect to aspect (a), prior to drying.

The canola protein isolate has a high protein content, in excess of about 90 wt %, preferably at least about 100 wt % protein (calculated as Kjeldahl N×6.25) and in substantially undenatured (as determined by diffusion scanning calorimetry).

The canola protein isolates provided herein contain a high proportion of 2S protein, preferably at least about 90 wt % and more preferably at least about 95 wt %, of the canola proteins in the isolates, and are substantially free from the 7S and 12S proteins.

EXAMPLES

Example 1

This Example illustrates the effect of elevated temperature of extraction of protein from canola oil seed meal on the profile of canola proteins in the extract solution.

15 g samples of vacuum desolventized canola oil seed meal (37.15% protein) were added to 150 ml samples of reverse osmosis (RO) water, an 0.1 M aqueous solution of NaCl, an 0.15 M aqueous solution of NaCl, an 0.2 M aqueous solution of NaCl, an 0.25 M aqueous solution of NaCl and an 0.5 M aqueous solution of NaCl respectively at a temperature of 85° C. The mixtures were stirred for 5 minutes while the temperature was maintained using a stirrer/hot plate.

The extracts were centrifuged for 10 minutes at 10,000 rpm and then filtered through a 25 μm fluted filter paper. The filtrate was further filtered through a 0.45 μm syringe filter.

The filtered extracts were analyzed for protein content (using a LECO FP528 Nitrogen Determinator), colour and protein profile (using analytical HPLC SEC BioSep 2000 and S3000 column).

The experiment was repeated using an extraction by 0.1 M NaCl solution at ambient temperature as a control and for comparison purposes. The results obtained are set forth in the following Tables 1 and 2:

TABLE 1

Meal Extracts at 85° C. Compared to an Ambient Extract

| Extract | A330 | A390 | LECO Protein (%) | Apparent Extractability (%) |
|---|---|---|---|---|
| 85° C. RO water extract | 89.9 | 4.34 | 0.48 | 12.93 |
| 85° C. 0.1M NaCl extract | 91.1 | 4.52 | 1.09 | 29.35 |
| 85° C. 0.15M NaCl extract | 94.8 | 4.51 | 1.11 | 29.88 |
| 85° C. 0.2M NaCl Extract | 114.0 | 5.15 | 1.24 | 33.38 |
| 85° C. 0.25M NaCl Extract | 110.7 | 5.51 | 1.26 | 33.92 |
| 85° C. 0.5M NaCl Extract | 130.3 | 13.99 | 1.46 | 39.30 |
| Control ambient extract 0.10M NaCl | 96.7 | 5.25 | 1.83 | 49.00 |

TABLE 2

Protein Profile of Extractions

| Sample: | % 2S | % 7S | % 12S |
|---|---|---|---|
| 85° C. RO ext | 83.8% | 12.5% | 3.8% |
| 85° C. 0.1M ext | 93.9% | 3.9% | 2.1% |
| 85° C. 0.15M ext | 98.2% | 0.9% | 0.9% |
| 85° C. 0.20M ext | 88.2% | 5.5% | 6.2% |
| 85° C. 0.25M ext | 86.9% | 7.2% | 5.9% |
| 85° C. 0.5M ext | 64.8% | 35.2% | 0.0% |
| amb.ext | 42.4% | 55.9% | 1.7% |

As may be seen from the results presented in Table 1, the use of an elevated temperature of extraction does not seem to influence colour determined at A330 (phenolics) and A390 (colour), indicating that no additional oxidation of phenolics occurs at the elevated temperatures.

The apparent extractability of the RO water at 85° C. was substantially lower than the saline extractions, indicating that the presence of salt during the extraction step beneficially improves the extractability even at elevated temperatures.

The apparent extractability for the high temperature saline extractions is in average about 32%, less than the extraction effected at ambient temperature but, as can be seen from Table 2, the majority of the protein extracted at the elevated temperature is the 2S protein.

Example 2

This Example sets forth a series of trials of a procedure for the processing of canola oil seed meal using a double extraction procedure.

A set of trials was carried out in which aqueous canola oil seed meal was initially extracted with water and subsequently with aqueous saline solution. The results of such series of trials are set forth herein.

(a) Trial 1

15 g of canola oil seed meal (batch A) were extracted at 60° C. and 10% w/v with 150 ml water preheated to 65° C. and added to the seed. The latter extract was subtracted from the spent meal by centrifugation at 10,000 g for 10 minutes and, after separation of the supernatant, the weight of the wet meal (37 g) and bound water (22 g) in the pellet was determined. Sufficient (128 ml) of 0.25 M NaCl was then added to bring the concentration back to 10% w/v and the sample was mixed with an overhead stirrer for 30 minutes at 220 rpm at room temperature. The saline extract was separated from the spent meal by centrifugation at 10,000 g for 10 minutes. Samples of the clarified water extract and saline extract were filtered with a 0.45 μm pore size filter and the samples analyzed for free phenolics (A330), visible colour (A 390), protein content (LECO) and protein profile (SEC HPLC). The protein profile of the water extract was also reanalyzed after overnight storage in the refrigerator to precipitate 7S protein.

Although lower in protein content, the secondary saline extract was clearly cleaner and less coloured than the initial water extract (Table 3).

TABLE 3

Analytical results for water and saline extracts

| Sample | A330 | A390 | % protein | % HPLC non-protein peak area |
|---|---|---|---|---|
| 60° C. water extract | 133.9 | 5.51 | 1.79 | 80.47 |
| Saline extract | 35.3 | 1.80 | 1.12 | 71.25 |

The initial water extraction favoured the solubilization of 7S protein, while the secondary saline extraction solubilized a majority of 2S protein (Table 4). Chilling the water extract overnight caused a large proportion of the 7S and 12S proteins to precipitate.

TABLE 4

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| 60° C. water extract | 2.4 | 74.3 | 23.3 |
| Saline extract | 2.9 | 32.3 | 65.0 |
| Chilled water super | 1.5 | 42.1 | 56.4 |

(b) Trial 2:

150 g of canola oil seed meal (batch A) was extracted at 60° C. and 10% w/v with 1500 ml water for 5 min with an overhead stirrer. The water extract was separated from the spent meal by centrifugation at 7100 g for 10 min and the weight of wet meal (392 g) and bound water (242 g) in the pellet was determined. Sufficient 0.2M NaCl (1258 ml) was then added to bring the concentration back to 10% w/v and the sample was mixed with an overhead stirrer for 30 min at room temperature. The saline extract was separated from the spent meal by centrifugation at 7100 g for 10 min and then filtered by two passes through #3 filter pads. The clarified saline extract was then processed using two 10,000 MWCO Vivaflow HY membrane (stabilizer cellulose) units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S, which was removed by centrifugation at 8000 g for 15 min. The concentrate was then freeze dried and given the designation 'C200H'.

The water extract was chilled overnight at 4° C. and then the precipitate collected by centrifugation at 7100 g for 15 min at 5° C. The collected solids were then freeze dried.

Various samples were analyzed for free phenolics (A330), visible colour (A390), protein content (LECO) and protein profile (SEC HPLC). Final products were analyzed for dry colour using a Minolta colourimeter and solutions were also prepared for wet colour analysis. Protein powder (0.7 g) was combined with 0.1M NaCl or water (10 ml) using a vortex mixer. The sample was then centrifugated at 8000 g for 10 min and the protein content of the supernatant determined by LECO. An aliquot (8 ml) of the supernatant was transferred to a small beaker and sufficient saline or water was added to adjust the protein content to 5%.

As in Trial 1, the secondary saline extract was cleaner and less coloured than the initial water extract (Table 5). Chilling the initial water extract caused just over half of the total protein to precipitate.

TABLE 5

Analytical results for water and saline extracts

| Sample | A330 | A390 | % protein | % HPLC non-protein peak area |
| --- | --- | --- | --- | --- |
| 60° C. water extract | 128.9 | 5.45 | 2.06 | 80.46 |
| Saline extract | 21.3 | 1.24 | 0.90 | 70.84 |
| Chilled water super | 136.0 | 4.66 | 1.02 | 91.30 |

Again the initial water extraction favoured the solubilization of 7S protein, while the secondary saline extraction solubilized a majority of 2S protein (Table 6). Heat treating the diafiltration (DF) retentate successfully removed the bulk of the remaining 7S and 12S protein. Chilling the water extract overnight caused a large proportion of the 7S and 12S proteins to precipitate.

TABLE 6

Protein profiles of various samples

| Sample | Proportion of protein peak area assigned to 12S (%) | Proportion of protein peak area assigned to 7S (%) | Proportion of protein peak area assigned to 2S (%) |
| --- | --- | --- | --- |
| 60° C. water extract | 2.3 | 75.2 | 22.5 |
| Saline extract | 1.2 | 30.8 | 68.0 |
| Heated DF ret centrate | 0.8 | 1.5 | 97.7 |
| Chilled water super | 1.4 | 43.5 | 55.1 |

The 'C200H' formed in this trial had good dry colour and acceptable wet colour (Table 7). Protein content of the powder (w.b.) was 93.90 wt %, confirming that the sample was an isolate. The cold precipitate 7S/12S was a fairly dark yellow powder but had an acceptable wet colour. Despite the relatively dark colour of the precipitated 7S/12S product, the purity of the product was very high when tested by LECO. The protein content of this sample (w.b.) was determined to be 103.49 wt %. Chromatographic analysis of the 7S/12S precipitate wet colour sample showed contamination with less than 4% protein peak area due to 2S protein and a non-protein peak area of about 25%. This is a fairly low concentration of contaminants considering that no purification steps were undertaken other than the precipitation.

TABLE 7

Dry colour of final products of Trial 2

| Sample | L | a | b |
| --- | --- | --- | --- |
| 'C200H' | 88.52 | −2.81 | 19.36 |
| Cold ppt 7S/12S | 66.79 | 0.25 | 35.15 |

(c) Trial 3:

150 g of canola oil seed meal (batch A) were extracted at 10% w/v with 1500 ml water at ambient temperature for 30 min with an overhead stirrer. The water extract was separated from the spent meal by centrifugation at 7100 g for 10 min and the weight of wet meal (366 g) and bound water (216 g) determined. Sufficient 0.2M NaCl (1284 ml) was then added to bring the concentration back to 10% w/v and the sample was mixed with an overhead stirrer for 30 min at room temperature. The saline extract was separated from the spent meal by centrifugation at 7100 g for 10 min and then filtered by two passes through #3 filter pads. The clarified saline extract was then processed using two 10000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S proteins, which was removed by centrifugation at 8000 g for 15 min. The centrate was then freeze dried and given the designation 'C200H—saline'.

The water extract was chilled overnight at 4° C. and then the precipitate collected by centrifugation at 7100 g for 15 min at 5° C. The collected solids were then freeze dried. The supernatant was filtered using #3 filter pads then processed using two 10000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S proteins, which was removed by centrifugation at 8000 g for 15 min. The centrate was then freeze dried and given the designation 'C200H—water'. Various samples were analyzed as detailed for Trial 2.

As in the previous trial, the secondary saline extract was cleaner and less coloured than the initial water extract (Table 8). However, the use of ambient water instead of hot water solubilized less nitrogen and slightly fewer contaminants. This water extract was more highly coloured than the hot water extracts, according to the A390 reading. Chilling the water extract precipitated less protein than when the 60° C. extract was chilled in Trial 2.

TABLE 8

Analytical results for water and saline extracts

| Sample | A330 | A390 | % protein | % HPLC non-protein peak area |
|---|---|---|---|---|
| ambient water extract | 123.3 | 6.00 | 1.66 | 80.18 |
| Saline extract | 27.1 | 1.73 | 0.86 | 71.76 |
| Chilled water super | 90.2 | 3.73 | 0.98 | 89.47 |

Ambient water extraction of the meal did not solubilize as much 7S protein as did the hot water extraction. As a result a higher proportion of 7S and 12S proteins ended up in the saline extract (Table 9). However, the 7S and 12S proteins were successfully removed in the heat treatment of the diafiltration retentate. Chilling the ambient water extract did precipitate 7S and 12S proteins, but not as much as when a hot water extract was chilled. Surprisingly, heat treatment was less effective at removing the 7S and 12S proteins from the diafiltered retentate prepared from the water process stream.

TABLE 9

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| Ambient water extract | 1.9 | 72.4 | 25.7 |
| Saline extract | 2.4 | 78.1 | 59.5 |
| Heated DF ret centrate - saline | 0.8 | 0.7 | 98.5 |
| Chilled water supernatant | 1.3 | 48.3 | 50.4 |
| Heated DF ret centrate - water | 0.8 | 9.6 | 89.6 |

The colour of the 'C200H' produced from the saline stream was only slightly lighter than the colour of the 'C200H' from the water stream (Table 9). Neither sample had as nice a colour as when hot water was used in the initial extraction (trial 2). The purity of the 'C200H' produced from the water stream (72.78% protein w.b.) was much poorer than the 'C200H' produced from the saline stream (96.68% protein w.b.). The HPLC chromatogram for the saline derived product (16.4% non protein peak area) was also cleaner than the chromatogram for the water derived product (27.9% non-protein peak area). The level of contaminants in the water extract thus was higher than the saline extract. Therefore, the water extract would require more extensive diafiltration for purification. The chill precipitated 7S and 12S protein obtained in this trial was slightly lighter than that obtained in the previous trial, perhaps because the ambient water extraction solubilized fewer impurities than the hot water extraction. The purity of the product was again very high with a protein content of 102.72% (w.b.).

TABLE 10

Dry colour of final products of Trial 3

| Sample | L | a | b |
|---|---|---|---|
| 'C200H' - saline | 86.04 | −2.96 | 22.91 |
| 'C200H' - water | 85.89 | −2.79 | 24.60 |
| Cold ppt 7S | 68.92 | −0.16 | 38.34 |

(d) Trial 4:

200 g of canola oil seed meal (batch B) were extracted at 10% w/v with water (2000 ml) at ambient temperature for 30 min with an overhead stirrer. The water extract was separated from the spent meal by centrifugation at 7100 g for 10 min and the weight of wet meal (639 g) and bound water (439 g) determined. Sufficient 0.25M NaCl (1561 ml) was then added to bring the concentration back to 10% w/v and the sample was mixed with an overhead stirrer for 30 min at room temperature. The saline extract was separated from the spent meal by centrifugation at 7100 g for 10 min and then filtered by two passes through #3 filter pads. The clarified saline extract was then processed using two 10000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S proteins, which were removed by centrifugation at 8000 g for 15 min. The centrate was then split into two portions with one stirred with 1 wt % powdered activated carbon for 30 min and the other half of the sample untreated. Both samples were centrifuged at 8000 g for 10 min, filtered with a 0.45 μm pore size syringe filter and then freeze dried and given the designations 'C200H' (no carbon) and 'C200HC' (carbon treated). The initial water extract was not processed in this trial. Various samples were analyzed as detailed for Trial 2.

As in the other trials, the secondary saline extract was cleaner and less coloured than the initial water extract (Table 11).

TABLE 11

Analytical results for water and saline extracts

| Sample | A330 | A390 | % protein | % HPLC non-protein peak area |
|---|---|---|---|---|
| ambient water extract | 104.5 | 4.93 | 1.02 | 85.37 |
| saline extract | 32.1 | 1.35 | 0.72 | 69.32 |

Again the initial water extraction favoured the solubilization of 7S protein, but the secondary saline extraction solubilized similar proportions of both protein classes (Table 12). The water extraction did not remove as much protein as in the other trials, which was likely a reflection of the different meal batches. Heat treating the diafiltration retentate successfully removed the bulk of the remaining 7S and 12S proteins. Carbon treating the resulting centrate did not alter the protein profile. Carbon treatment did reduce the HPLC non-protein peak area from 15.76% to 4.82%.

TABLE 12

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| ambient water extract | 2.0 | 77.9 | 20.1 |
| Saline extract | 4.2 | 44.7 | 51.1 |
| Heated DF ret centrate | 1.9 | 0.5 | 97.6 |

TABLE 12-continued

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| Heated DF ret centrate - carbon | 1.9 | 0.5 | 97.6 |

Carbon treatment of the heat treated diafiltration retentate centrate did improve the colour of the resulting product (Table 13). The dry colour of the 'C200HC' was slightly lighter and notably less yellow than the 'C200H'. An improvement was also noted in the wet colour samples.

TABLE 13

Dry colour of final products of Trial 4

| Sample | L | a | b |
|---|---|---|---|
| 'C200H' | 83.64 | −1.61 | 22.69 |
| 'C200HC' | 84.76 | −1.64 | 17.64 |

(e) Trial 5:

200 g of sifted canola oil seed meal (batch B) were extracted at 10% w/v with water (2000 ml) at ambient temperature for 30 min with an overhead stirrer. The water extract was separated from the spent meal by centrifugation at 7100 g for 10 min and the weight of wet meal (648 g) and bound water (448 g) determined. Sufficient 0.25M NaCl (1552 ml) was then added to bring the concentration back to 10% w/v and the sample was mixed with an overhead stirrer for 30 min at room temperature. The saline extract was separated from the spent meal by centrifugation at 7100 g for 10 min and then filtered by passing through #2 and #3 filter pads. The clarified saline extract was then processed using two 10,000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S proteins, which were removed by centrifugation at 8000 g for 15 min. The centrate was then split into two portions with one stirred with 1% powdered activated carbon for 30 min and the other half of the sample untreated. Both samples were centrifuged at 8000 g for 10 min, filtered with a 0.45 μm pore size syringe filter and then freeze dried and given the designations 'C200H' (no carbon) and 'C200HC' (carbon treated). The initial water extract was not processed in this trial. Various samples were analyzed as detailed for Trial 2.

As in the other trials, the secondary saline extract was cleaner and less coloured than the initial water extract (Table 14). Use of sifted meal instead of regular meal with a higher content of hulls resulted in more protein, colour and phenolics being extracted.

TABLE 14

Analytical results for water and saline extracts

| Sample | A330 | A390 | % protein | % HPLC non-protein peak area |
|---|---|---|---|---|
| ambient water extract | 111.1 | 6.11 | 1.27 | 85.12 |
| saline extract | 41.1 | 1.74 | 0.89 | 70.59 |

Again the initial water extraction proportionally favoured the solubilization of 7S protein, but with the limited extractability, the secondary saline extraction solubilized similar proportions of both proteins (Table 15). Heat treating the diafiltration retentate successfully removed the bulk of the remaining 7S protein. Carbon treating the resulting centrate did not alter the protein profile. Carbon treatment did reduce the HPLC non-protein peak area from 10.94% to 1.58%.

TABLE 15

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| ambient water extract | 2.2 | 73.5 | 24.2 |
| Saline extract | 4.7 | 42.3 | 53.0 |
| Heated DF ret centrate | 1.1 | 0.5 | 98.4 |
| Heated DF ret centrate - carbon | 1.1 | 0.5 | 98.4 |

Carbon treatment of the heat treated diafiltration retentate centrate did improve the colour of the resulting product, but not as well as in the previous trial (Table 16). In this trial the dry colour of the 'C200HC' was less yellow than the 'C200H' but the carbon treated product was slightly more red and darker than the untreated sample. Carbon treatment improved the wet colour, but again a stronger improvement was seen in Trial 4.

TABLE 16

Dry colour of final products of Trial 5

| Sample | L | a | b |
|---|---|---|---|
| 'C200H' | 84.31 | −1.61 | 22.17 |
| 'C200HC' | 83.29 | −1.32 | 18.39 |

(f) Trial 6:

150 g of canola oil seed meal (batch B) were extracted at 10% w/v with water (1500 ml) at 60° C. for 15 min with an overhead stirrer. The water extract was separated from the spent meal by centrifugation at 5200 g for 10 min and the weight of wet meal (458 g) and bound water (308 g) determined. Sufficient 0.25M NaCl (1192 ml) was then added to bring the concentration back to 10% w/v and the sample was mixed with an overhead stirrer for 30 min at room temperature. The saline extract was separated from the spent meal by centrifugation at 5200 g for 10 min and then filtered with #3 filter pads. The clarified saline extract was then processed using two 10000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 5200 g for 10 min before re-concentration. The diafiltration retentate was heat treated at 85° C. for 10 min to precipitate 7S and 12S proteins, which were removed by centrifugation at 8000 g for 15 min. The centrate was then freeze dried and given the designation 'C200H'. The initial water extract was not processed in this trial. Various samples were analyzed as detailed for Trial 2.

As in the other trials, the secondary saline extract was cleaner and less coloured than the initial water extract (Table 17). The longer 60° C. water extraction may have slightly improved the quality of the saline extract, but the effect did not appear to be significant.

TABLE 17

Analytical results for water and saline extracts

| Sample | A330 | A390 | % protein | % HPLC non-protein peak area |
|---|---|---|---|---|
| 60° C. water extract | 89.1 | 4.44 | 1.32 | 83.97 |
| saline extract | 19.1 | 1.07 | 0.75 | 70.57 |

The protein profiles of various samples are shown in Table 18. It appeared that a longer water extraction at 60° C. solubilized more 7S and 12S proteins than previous extractions of the same batch of meal. This is desirable as it reduced the 7S/12S content of the saline extract, making it easier to prepare a sample of purified 2S protein.

TABLE 18

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| 60° C. water extract | 3.5 | 81.1 | 15.5 |
| Saline extract | 2.0 | 27.7 | 70.3 |
| Heated DF ret centrate | 1.5 | 0.4 | 98.1 |

The dry colour of this sample was average (Table 19) and the wet colour was fair, but not as good as previously seen for carbon treated samples.

TABLE 19

Dry Colour of Final Products of Trial 6

| Sample | L | a | b |
|---|---|---|---|
| 'C200H' | 83.32 | −1.12 | 21.56 |

(g) Trial 7:

160 g of canola oil seed meal (batch B) with 1 wt % powdered activated carbon (16 g) were extracted at 10% w/v with water (1600 ml) at 60° C. for 5 minutes with an overhead stirrer. The water extract was separated from the spent meal and carbon by centrifugation at 7100 g for 10 min and the weight of wet meal/carbon (533 g) and bound water (357 g) determined. Sufficient 0.2M NaCl (1243 ml) was then added to bring the concentration back to 10% w/v. Another 16 g of fresh powdered activated carbon was also added to the system and the sample was mixed with an overhead stirrer for 30 min at room temperature. The saline extract was separated from the spent meal by centrifugation at 7100 g for 10 min and then filtered with #3 filter pads. The clarified saline extract was then processed using two 10,000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentration. The diafiltration retentate was heat treated at 85° C. for 10 min to precipitate 7S and 12S proteins, which were removed by centrifugation at 8000 g for 15 min. The centrate was then freeze dried and given the designation 'C200H'. The initial water extract was not processed in this trial. Various samples were analyzed as detailed for Trial 2.

Inclusion of carbon in the extraction steps greatly reduced the colour and impurity content of the process streams (Table 20).

TABLE 20

Analytical results for water and saline extracts

| Sample | A330 | A390 | % protein | % HPLC non-protein peak area |
|---|---|---|---|---|
| 60° C. water extract | 7.86 | 0.55 | 1.07 | 45.18 |
| saline extract | 0.29 | 0.10 | 0.44 | 2.35 |

The protein profiles of various samples are shown in Table 21. The proportion of proteins in the water extract was very similar to that seen in Trial 6. However, the proportion of protein doses in the saline extract was much more even than in Trial 6 where 2S protein was clearly favoured. An explanation for this could be the lower level of protein extractability by the water phase in this trial and perhaps losses of 2S protein to the carbon. However, carbon did not change the protein profile when applied in Trials 4 and 5.

TABLE 21

Protein profiles of various samples

| Sample | Proportion of protein peak area assigned to 12S (%) | Proportion of protein peak area assigned to 7S (%) | Proportion of protein peak area assigned to 2S (%) |
|---|---|---|---|
| 60° C. water extract | 3.5 | 83.0 | 13.5 |
| Saline extract | 3.3 | 42.9 | 53.8 |
| 'C200H' | 3.2 | 0.1 | 96.7 |

This sample had excellent dry and wet colour (Table 22). The LECO result for the 'C200H' powder was only 89.3% w.b., but on a dry basis the sample was likely an isolate. The concentration of non-protein impurities according to HPLC on the final product was only 1.1%. Therefore, the majority of non protein species present in the sample do not absorb at 280 nm. Salt would be the most likely of these compounds. Additional diafiltration with water may be used to remove this salt and improve the protein content of the final product.

TABLE 22

Dry colour of final products of Trial 7

| Sample | L | a | b |
|--------|-------|-------|-------|
| 'C200H' | 89.67 | −1.87 | 15.47 |

The results of the Trials 1 to 7 demonstrate that a double extraction procedure carried out on a canola oil seed meal produced 7S protein-rich and 2S protein-rich streams.

Example 3

This Example sets forth a series of trials of the double extraction procedure of Example 2, in which multiple water extractions were carried out prior to saline extraction.

The results of this series of trials are set forth herein. It is noted that, industrially, a water extraction of the seed meal would be performed using a counter-current extractor. Such processes expose the meal to the equivalent of a large number of individual washings.

Trial 1:

15 g of canola seed meal (batch B) were extracted with water (150 ml) at 60° C. for 5 minutes. The water was pre-heated to 65° C. and then mixed with the meal using an orbital shaker operating at 220 rpm. Extract was separated from the spent meal by centrifugation at 10,000 g for 10 min. The extract was decanted off and the wet meal was recovered, weighed and the volume of entrapped water calculated. Sufficient 65° C. water to bring the volume back to 150 ml was then added to the spent meal and the extraction repeated as detailed above. This process was repeated until four water extractions had been performed. A fifth extraction was then performed with room temperature 0.5M NaCl. Sufficient saline was added to bring the volume back to 150 ml and then the extraction performed by shaking the sample at 220 rpm for 30 min at room temperature. Table 23 shows the volume of water or saline added for each extraction. Note that cohesive pellets were not obtained when centrifuging after the second and third extractions. Therefore, more solvent was retained so as not to lose meal when decanting the samples. Theoretically, more contaminants could have been extracted if the maximum volume of spent water could have been removed and replaced with fresh water.

TABLE 23

Volume of extraction fractions

| Extraction no. | Wt meal (g) | Vol. entrapped water (ml) | Vol. added solvent (ml) |
|----------------|-------------|---------------------------|-------------------------|
| 1 | 15 | 0 | 150 |
| 2 | 40 | 25 | 125 |
| 3 | 57 | 42 | 108 |
| 4 | 78 | 63 | 87 |
| 5 | 40 | 25 | 125 |

The pH, conductivity and brix of extract samples were measured and then the samples filtered with a 0.45 um pore size syringe filter and tested for free phenolics (A330), visible colour (A390), protein content (LECO), and protein profile (SEC HPLC).

Successive water extractions did remove substantial amounts of protein and impurities (Table 24). The saline extract produced in this trial was much cleaner than the saline extracts produced in single water extraction trials reported in Example 2. In those trials, the saline extract was found to contain approximately 70% non-protein peak area by HPLC. However, the saline extract from the trial with one water extract followed by a saline extract, both with carbon treatment had a much lower A330 (0.29), A390 (0.10) and % HPLC non-protein peak area (2.34%) than the current trial. These differences suggests that the multiple water extractions may not produce a saline extract clean enough to get the desired product colour.

TABLE 24

Analytical results for Trial 1 extracts

| Sample | pH | Cond. (mS) | Brix | A330 | A390 | Protein (%) | % HPLC peak area due to non-protein |
|--------|------|------|------|-------|-------|------|-------|
| Water extract #1 | 5.86 | 2.50 | 3.3 | 106.6 | 4.73 | 1.21 | 84.42 |
| Water extract #2 | 6.06 | 0.825 | 0.7 | 23.1 | 1.53 | 0.26 | 91.61 |
| Water extract #3 | 6.16 | 0.415 | 0.4 | 9.80 | 0.811 | 0.08 | 91.73 |
| Water extract #4 | 6.26 | 0.269 | 0.3 | 5.73 | 0.518 | 0.03 | 91.89 |
| 0.5M NaCl extract | 6.01 | 33.5 | | 7.37 | 0.513 | 0.62 | 23.62 |

The 7S protein was more readily extracted with hot water than the 2S protein (Table 25). As expected, the saline extract was rich with 2S protein. It is estimated that approximately ⅓rd of the total extracted 2S protein went to the lower purity water stream with the majority of the 7S/12S proteins and the impurities. It is desirable to keep as much 2S protein as possible in the high purity stream. The limit of acceptability for losses of 2S protein with the water phase (recovered as a lower quality product) and in fact the value of the entire multiple extraction scheme depends on the quality and value of the 2S protein coming from the saline stream.

TABLE 25

Protein profile of Trial 1 extracts

| Sample | Proportion of protein peak area assigned to 12S (%) | Proportion of protein peak area assigned to 7S (%) | Proportion of protein peak area assigned to 2S (%) |
|--------|------|------|------|
| Water extract #1 | 2.4 | 80.6 | 17.0 |
| Water extract #2 | 3.3 | 86.6 | 10.1 |
| Water extract #3 | 8.3 | 83.3 | 8.4 |
| Water extract #4 | 8.7 | 81.0 | 10.3 |
| 0.5M NaCl extract | 5.1 | 20.0 | 74.9 |

Trial 2:

150 g of canola seed meal (batch B) was extracted with water (1500 ml) at 60° C. for 5 minutes. The water was pre-heated to 65° C. and then mixed with the meal using an overhead stirrer. Extract was separated from the spent meal by centrifugation at 7100 g for 10 min. The extract was decanted off and the wet meal was recovered, weighed and the volume of entrapped water calculated. Sufficient 65° C. water to bring the volume back to 1500 ml was then added to the spent meal and the extraction repeated as detailed above. This process was repeated until 4 water extractions had been performed. A fifth extraction was then performed with room temperature 0.2M NaCl. A lower salt concentration was chosen than in Trial 1 as the salt had to be removed by diafiltration and time only allowed for processing with five diafiltration volumes. Sufficient 0.2M NaCl was added to bring the volume back to 1500 ml and then the extraction performed by mixing the sample with an overhead stirrer for 30 min at room temperature. Table 26 shows the volume of water or saline added for each extraction.

TABLE 26

Volume of extraction fractions

| Extraction no. | Wt meal (g) | Vol. entrapped water (ml) | Vol. added solvent (ml) |
|---|---|---|---|
| 1 | 150 | 0 | 1500 |
| 2 | 430 | 280 | 1220 |
| 3 | 459 | 309 | 1191 |
| 4 | 466 | 316 | 1184 |
| 5 | 426 | 276 | 1224 |

The saline extract was separated from the spent meal by centrifugation at 7100 g for 10 min and then filtered through #3 filter pads. The clarified saline extract was then processed using two 10000 MWCO Vivaflow HY membrane units joined in parallel. The extract was concentrated and then diafiltered with 5 volumes of reverse osmosis (RO) purified water. Addition of the diafiltration water resulted in the generation of a precipitate that was removed by centrifugation at 7100 g for 10 min before re-concentrating. The diafiltration retentate was heat treated at 85° C. for 10 min to precipitate 7S and 12S proteins, which were removed by centrifugation at 8000 g for 15 min. The centrate was then freeze dried and designated 'C200H'.

Various samples were analyzed for free phenolics (A330), visible colour (A390), protein content (LECO) and protein profile (SEC HPLC). Final products were analyzed for dry colour using a Minolta colourimeter and solutions were also prepared for wet colour analysis. Protein powder (0.7 g) was combined with 0.1M NaCl (10 ml) using a vortex mixer. The sample was then centrifuged at 8000 g for 10 min and the protein content of the supernatant determined by LECO. An aliquot (8 ml) of the supernatant was transferred to a small beaker and sufficient saline was added to adjust the protein content to 5%. The samples were then photographed.

The water extractions in this run appeared to remove roughly the same amount of protein, colour and impurities compared to Trial 1 (Table 27). The quality of the saline extract appeared slightly different with less protein, free phenolics, impurities and visible colour found in the extract of this trial. Since the analytical data for the water extracts appeared so similar, the differences in the saline extracts likely was due to differing salt concentrations.

TABLE 27

Analytical results for Trial 2 extracts

| Sample | pH | Cond. (mS) | Brix | A330 | A390 | Protein (%) | % HPLC peak area due to non-protein |
|---|---|---|---|---|---|---|---|
| Water extract #1 | 6.02 | 2.53 | 3.2 | 97.7 | 4.96 | 1.11 | 84.36 |
| Water extract #2 | 6.24 | 0.906 | 1.0 | 22.8 | 1.63 | 0.22 | 91.12 |
| Water extract #3 | 6.39 | 0.400 | 0.4 | 9.48 | 0.756 | 0.14 | 90.27 |
| Water extract #4 | 6.49 | 0.222 | 0.2 | 4.36 | 0.437 | 0.12 | 84.19 |
| 0.2M NaCl extract | 6.18 | 15.88 |  | 1.99 | 0.202 | 0.40 | 14.19 |

The protein profiles of the water extracts in this trial (Table 28) were similar to trial 1, but the saline extract was found to have a higher proportion of 2S protein. This was somewhat surprising as less salt was used in this trial and the increased salinity was believed to favour the extraction of 2S protein over 7S protein.

TABLE 28

Protein profile of trial 2 extracts

| Sample | Proportion of protein peak area assigned to 12S (%) | Proportion of protein peak area assigned to 7S (%) | Proportion of protein peak area assigned to 2S (%) |
|---|---|---|---|
| Water extract #1 | 2.2 | 81.5 | 16.3 |
| Water extract #2 | 4.6 | 86.3 | 9.1 |
| Water extract #3 | 11.7 | 83.4 | 4.9 |
| Water extract #4 | 18.9 | 73.1 | 8.0 |
| 0.2M NaCl extract | 2.2 | 8.1 | 89.7 |

Membrane processing the saline extract further purified it, with the % HPLC non-protein peak area for the diafiltration retentate found to be only 2.3%. This is lower than typically seen for single water extraction trials (see Example 2).

The dry colour of the 'C200H' produced in this trial is shown in Table 29. This colour is very similar to that seen in other double extraction trials with the same meal. The use of powdered carbon along with the double extraction produced a 'C200H' with a lightness value of almost 90 and less red and yellow notes than in the product of this trial.

TABLE 29

Dry colour of Trial 2 product

|  | L | a | b |
|---|---|---|---|
| 'C200H' - Trial 2 | 83.53 | −1.07 | 19.20 |

The wet colour of the 'C200H' produced in trial 2 was also no better than seen in other double extraction trials (60° C. water) without adsorbent and was definitely darker than the sample produced with adsorbent.

The results of these trials in comparison to those in Example 2 indicate that multiple water extractions of the meal prior to saline extraction appeared to eliminate additional impurities (no adsorbent) but did not have a large impact on final product quality.

Example 4

This Example illustrates the preparation of an isolated 2S protein product from ultrafiltration retentate.

40 kg of canola meal was added to 400 L of 0.15M NaCl solution at ambient temperature, are agitated for 30 minutes to provide an aqueous protein solution. The residual canola meal was removed and the resulting protein solution was clarified by centrifugation and filtration to produce 139 L of filtered protein solution having a protein content of 1.87% by weight.

A 139 L aliquot of the protein extract solution was reduced in volume to 8.9 L by concentration on a PVDF membrane having a molecular weight cutoff of 30,000 daltons. A 5 L aliquot of the concentrated protein solution was then diafiltered with 24.8 L of 0.15M NaCl solution on a PES membrane having a molecular weight cutoff of 100,000 daltons. The diafiltered retentate was then pasteurized at 60° C. for 10 minutes.

A sample of the diafiltered and pasteurized ultrafiltration (UF1) retentate was obtained. The protein content of this retentate was 18.30 wt %. It was thought that the high protein concentration combined with the high proportion of 7S present in a UF1 retentate would result in gelation rather than just precipitation upon heating. As a result, the protein concentration of the sample was adjusted prior to heat treatment by combining 100 ml retentate with 100 ml of 0.1M NaCl.

The diluted sample was heat treated at 85° C. for 10 minutes and then rapidly cooled in cold water to below 30° C. The sample was then centrifuged at 10200 g for 15 min. After centrifugation a pellet was obtained as well as some floating precipitate particles. The supernatant was decanted and the floating particles removed by filtration through a 25 um pore size filter paper. The recovered supernatant (120 ml) was concentrated on a Vivaflow 10000 HY membrane unit, then diafiltered with 10 volumes of reverse osmosis purified water to remove salt. The diafiltered retentate was then freeze dried and given designation C500H.

Various samples were analyzed for free phenolics (A330), visible colour (A390), protein content (LECO) and protein profile (SEC HPLC). The final product was analyzed for moisture content using an oven drying method, dry colour using a Minolta colourimeter and a solution was also prepared for wet colour analysis. Protein powder (0.7 g) was combined with water (10 ml) using a vortex mixer. The sample was then centrifuged at 7800 g for 10 min and the protein content of the supernatant determined by LECO. An aliquot (8 ml) of the supernatant was transferred to a small beaker and sufficient water was added to adjust the protein content to 5 wt %. The sample was then photographed.

Heat treatment of the UF1 retentate successfully removed the bulk of the 7S and 12S proteins from the sample. The proportion of HPLC protein peak area due to 7S and 12S in the initial retentate was 61.4% and 2% respectively. This was reduced to 4.4% 7S and 0.4% 12S in the supernatant of the heat treated sample. The final product obtained was an isolate with a protein content (wet basis) of 90.32% and a moisture content of 4.82%, resulting in a protein content (dry basis) of 94.89%. The dry colour of the product was a little darker than has historically been seen for C200H products (Table 30).

TABLE 30

Dry colour for C500H produced from UF1 retentate

| Sample | L | a | b |
| --- | --- | --- | --- |
| C500H | 80.84 | −1.12 | 22.32 |

The wet colour of the product was quite good, although perhaps a little bit darker than has been seen for C200H. The sample was slightly hazy.

As may be seen from the results set forth herein, a canola protein isolate consisting essentially of 2S protein was successfully generated from UF1 retentate.

Example 5

This Example illustrates heat treatment of canola protein extract solution formed from canola oil seed meal.

50 g of canola oil seed meal (SB062) was extracted with 1500 ml of 0.1M NaCl for 30 minutes at room temperature using an overhead stirrer. The mixture was centrifuged at 7100 g for 10 min to separate the extract from the spent meal. The collected extract was heat treated at 85° C. for 10 min in a double boiler pot to precipitate 7S/12S. After the heat treatment, the sample was immediately cooled below 30° C. by submersion in a cold water bath. The precipitated solids were removed by centrifugation at 7100 g for 10 min and then the centrate was polished with #3 filter pads. The clarified centrate was then concentrated on a Vivaflow 10000 HY ultrafiltration unit and diafiltered with 10 volumes of reverse osmosis purified water. Addition of the diafiltration water resulted in the formation of some precipitate that was removed by centrifugation of the sample at 7100 g for 10 min prior to re-concentration. The diafiltered retentate was freeze dried to form the final product.

Various samples were analyzed for free phenolics (A330), visible colour (A390), protein content (LECO) and protein profile (SEC HPLC). The final product was analyzed for moisture content using an oven drying method, dry colour using a Minolta colourimeter and a solution was also prepared for wet colour analysis. Protein powder (0.8 g) was combined with water (10 ml) using a vortex mixer. The sample was then centrifuged at 7800 g for 10 min and the protein content of the supernatant determined by LECO. An aliquot (8 ml) of the supernatant was transferred to a small beaker and sufficient water was added to adjust the protein content to 5%. The sample was then photographed.

Heat treatment of the extract successfully removed the bulk of the 7S and 12S from the sample. The proportion of HPLC protein peak area due to 7S and 12S in the initial extract was 63.8% and 3.8% respectively. This was reduced to 2.0% 7S and 0.8% 12S in the centrate of the heat treated sample. The precipitate formed by heating the extract was readily removed by centrifugation. The final product obtained was an isolate with a protein content (wet basis) of 84.15% and a moisture content of 7.22%, resulting in a protein content (dry basis) of 90.70%. The dry colour of the product was slightly darker and redder than has historically been seen for the majority of isolated 2S products (Table 31).

TABLE 31

Dry colour for isolated 2S produced from heat treated extract

| Sample | L | a | b |
| --- | --- | --- | --- |
| 2S from heat treated extract | 80.60 | −0.57 | 22.34 |

SUMMARY OF THE DISCLOSURE

In summary of this disclosure, there are provided procedures for the preparation of canola protein isolate consisting essentially of the 2S canola protein and substantially free from the 7S and 12 S proteins. Modifications are possible within the scope of the invention.

What we claim is:

1. A method for production of a canola protein isolate consisting predominantly of the 2S canola protein, which comprises:
    extracting canola oil seed meal with an aqueous salt solution having an ionic strength of at least about 0.05 and a pH of about 5 to about 6.8 at an elevated temperature of about 80° to about 100° C. to preferentially extract the 2S protein from the canola oil seed meal in preference to the 7S and 12S proteins and to obtain a canola protein extract solution containing predominantly 2S protein,
    separating the canola protein extract solution from residual canola oil seed meal, and
    recovering from the canola protein extract solution a canola protein isolate having a protein content of at least about 90 wt % (N×6.25) and consisting predominantly of the 2S canola protein, wherein said recovering of the canola protein isolate is effected by concentrating the canola protein extract solution, wherein the concentrated canola protein extract solution is subjected to a heat treatment step so as to form a precipitate to decrease the proportion of the 7S and 12S protein in said solution by at least about 50 wt %, and wherein the precipitate is separated from the solution.

2. The method of claim 1, wherein said aqueous salt solution has an ionic strength of at least about 0.10 and a pH of about 5.3 to about 6.2 and said elevated temperature is about 80° to about 95° C.

3. The method of claim 1, wherein said canola protein extract solution has a canola protein profile which is:
    about 80 to about 100 wt % 2S protein,
    0 to about 10 wt % 7S protein, and
    0 to about 10 wt % 12S protein.

4. The method of claim 3, wherein said canola protein extract solution has a canola protein profile which is:
    about 85 to about 100 wt % 2S protein,
    0 to about 15 wt % 7S protein, and
    0 to about 5 wt % 12S protein.

5. The method of claim 1 wherein the canola protein isolate consisting predominantly of 2S protein has a protein content of at least about 100 wt %.

6. The method of claim 1, wherein the canola protein extract solution is concentrated to a protein concentration of at least about 50 g/L.

7. The method of claim 1, wherein the canola protein extract solution is concentrated to a protein concentration of about 100 g/L to about 400 g/L, preferably about 200 g/L to about 300 g/L.

8. The method of claim 7, wherein the concentrated aqueous canola protein extract is subjected to diafiltration using from about 2 to about 20 volumes of diafiltration medium.

9. The method of claim 8, wherein said diafiltration is carried out using about 5 to about 10 volumes of diafiltration medium.

10. The method of claim 9, wherein an antioxidant is present during at least part of the diafiltration step.

11. The method of claim 1, wherein the resulting concentrated canola protein extract solution is dried following the heat treatment step.

12. The method of claim 1, wherein said heat treatment is effected at a temperature of about 70° to about 100° C. for about 2 to about 30 minutes and to reduce the 7S and 12S protein contents by at least about 50 wt %.

13. The method of claim 12, wherein said heat treatment is effected at a temperature of about 75° to about 95° C. for about 5 to about 15 minutes and to reduce the 7S and 12S protein contents by at least about 75 wt %.

14. The method of claim 1 wherein said canola protein isolate consisting predominantly of 2S protein contains at least about 90 wt % 2S protein of the canola proteins present.

15. The method of claim 1 wherein said canola protein isolate consisting predominantly of 2S protein contains at least about 95 wt % 2S protein of the canola proteins present.

* * * * *